(12) United States Patent
Sahibzada

(10) Patent No.: US 7,823,438 B2
(45) Date of Patent: Nov. 2, 2010

(54) FLUID DETECTOR

(75) Inventor: Jörgen Sahibzada, Göteborg (SE)

(73) Assignee: Calectro AB, Vastra Frolunda (SE)

( * ) Notice: Subject to any disclaimer, the term of this patent is extended or adjusted under 35 U.S.C. 154(b) by 492 days.

(21) Appl. No.: 11/662,628

(22) PCT Filed: Jan. 5, 2006

(86) PCT No.: PCT/SE2006/000013

§ 371 (c)(1),
(2), (4) Date: Dec. 7, 2007

(87) PCT Pub. No.: WO2006/078204

PCT Pub. Date: Jul. 27, 2006

(65) Prior Publication Data

US 2008/0196479 A1    Aug. 21, 2008

(30) Foreign Application Priority Data

Jan. 24, 2005    (SE) .................................... 0500176

(51) Int. Cl.
G01N 1/20  (2006.01)
G01N 7/00  (2006.01)

(52) U.S. Cl. ................... 73/23.2; 73/863.81; 73/863.51

(58) Field of Classification Search ................... 73/23.2, 73/863.31, 863.21, 863.81, 863.51
See application file for complete search history.

(56) References Cited

U.S. PATENT DOCUMENTS

| 5,001,463 | A | | 3/1991 | Hamburger | 340/627 |
| 5,625,156 | A | * | 4/1997 | Serrels et al. | 73/863.51 |
| 5,834,657 | A | * | 11/1998 | Clawson et al. | 73/863.81 |
| 6,085,576 | A | | 7/2000 | Sunshine et al. | 73/29.01 |

(Continued)

FOREIGN PATENT DOCUMENTS

DE    20-2005-000060    4/2005

(Continued)

OTHER PUBLICATIONS

International Search Report (PCT/ISA/210).

(Continued)

*Primary Examiner*—Hezron Williams
*Assistant Examiner*—Tamiko D Bellamy
(74) *Attorney, Agent, or Firm*—Harness, Dickey & Pierce P.L.C.

(57) ABSTRACT

A device is disclosed for sensing a fluid, such as in a ventilation duct. In at least one embodiment, the device includes a sensing element, a housing accommodating the sensing element, and a supply duct and a discharge duct, which ducts at one end commucicate with the housing and which ducts at the other end communicate with an object that is to be sensed. In at least one embodiment, the housing is formed with a first passage portion for the fluid that is to be sensed; that the sensing element is positioned in the first passage portion; and that the supply duct opens into said first passage portion and that the discharge duct is connected to a discharge opening formed in the first passage portion and positioned at a considerable peripheral distance from the mouth of said supply duct in the first passage portion, so that the fluid that is to be sensed is actively made to pass the sensing element.

22 Claims, 3 Drawing Sheets

U.S. PATENT DOCUMENTS

| | | | |
|---|---|---|---|
| 6,432,288 B1 * | 8/2002 | Nielsen et al. | 204/424 |
| 6,470,732 B1 | 10/2002 | Breton | 73/23.31 |
| 7,089,811 B2 * | 8/2006 | Allmendinger | 73/863.51 |
| 2002/0195339 A1 | 12/2002 | Nakamura et al. | 204/428 |
| 2006/0027353 A1 | 2/2006 | Luthi et al. | 165/11.1 |

FOREIGN PATENT DOCUMENTS

| | | |
|---|---|---|
| EP | 1 624 295 | 2/2006 |
| FR | 1 480 257 | 5/1967 |
| FR | 2 391 742 | 12/1978 |
| GB | 1 137 039 | 12/1968 |

OTHER PUBLICATIONS

Extended Search Report dated Aug. 2, 2007 for corresponding European Application No. 06 70 0214.

* cited by examiner

FLUID DETECTOR

FIELD OF THE INVENTION

The present invention relates to a device for sensing a fluid, such as in a ventilation duct, comprising a sensing element, a housing accommodating the sensing element, and a supply duct and a discharge duct, which ducts at one end communicate with the housing and which ducts at the other end communicate with an object that is to be sensed.

BACKGROUND ART

When sensing, for instance, flue gases in a fluid, such as a fluid in a ventilation duct, it is important for the sensing to be reliable. As a rule, such sensing is done by part of the fluid being made to pass a smoke detector which is arranged outside the ventilation duct.

Different types of devices for such sensing are known, in which sensing occurs by fluid being diverted from the ventilation duct and being passed to a space that accommodates a smoke detector for sensing, after which the fluid is returned to the duct. If the smoke detector senses that there is flue gas in the fluid from the ventilation duct, the smoke detector emits, for instance, a signal which can be connected to an alarm, or which can constitute an initiation signal to close the duct system etc.

These prior-art devices for sensing a fluid frequently have a not quite satisfactory function as regards safe and reliable registration of small amounts of, for instance, flue gas in said fluid. Therefore there is a need to be able to sense a fluid, for instance, in a ventilation duct with sufficient accuracy.

SUMMARY OF THE INVENTION

An object of the present invention is to provide an alternative device for sensing a fluid, said device registering with great reliability the presence of, for instance, particles and/or gases in the fluid.

A further object of the present invention is to provide a device for sensing a fluid, which device has a compact and space-efficient construction.

Another object is to provide a device for sensing a fluid, which device is inexpensive to manufacture and easy to mount.

The above objects and other objects that will be evident from the following description are achieved by a device for sensing a fluid according to the appended claims.

According to one aspect of the present invention, a device is provided for sensing a fluid, such as in a ventilation duct, comprising a sensing element, a housing accommodating the sensing element, and a supply duct and a discharge duct, which ducts at one end communicate with the housing and which ducts at the other end communicate with an object that is to be sensed. The device for sensing a fluid is characterised in that the housing is formed with a first passage portion for the fluid that is to be sensed;

that the sensing element is positioned in the first passage portion; and that the supply duct opens into said first passage portion and that the discharge duct is connected to a discharge opening formed in the first passage portion and positioned at a considerable peripheral distance from the mouth of said supply duct in the first passage portion, so that the fluid that is to be sensed is actively made to pass the sensing element.

By arranging said supply duct and discharge duct at a considerable peripheral distance from each other, safe flow of the fluid through the sensor is provided, which in turn results in reliable sensing of the fluid. In a preferred embodiment, the supply duct and the discharge duct are arranged substantially opposite each other.

In one embodiment, the mouth of the supply duct in the first passage portion is facing a throughput portion of the sensing element to provide reliable sensing of the fluid. In this way, the fluid supplied to the device will be forced to pass the sensing element, and substantially the whole amount of supplied fluid will be sensed. Furthermore the mouth of the supply duct in the first passage portion is in one embodiment arranged in the vicinity of said throughput portion of the sensing element, resulting in essentially direct supply of the fluid to the sensing element. The path of the fluid through the housing from the mouth of the supply duct up to the sensing element will thus be substantially straight without deflections or other interruptions.

Preferably the housing is provided with a second passage portion which is substantially shielded from the first passage portion and which extends between said discharge opening in the first passage portion and the discharge duct. Furthermore said second passage portion is in one embodiment arranged as a passage duct which extends peripherally outside the first passage portion from said discharge opening to said discharge duct. With such a design, the fluid can preferably be returned towards the object, for instance a ventilation duct, through the second passage portion after having passed the sensing element. It will be appreciated that it is possible to design this second passage portion in various ways as essentially return of the fluid is involved after it has passed the sensor in the first passage portion. It will also be appreciated that a reversible device for sensing a fluid is involved, where the flow direction through the device can be reversed with the function maintained.

A mouth of the discharge duct is preferably positioned in the vicinity of the mouth of said supply duct at a considerable peripheral distance from the discharge opening. This allows easy connection of both ends of the supply duct and the discharge duct to, respectively, the housing and the object containing the fluid that is to be sensed.

In a preferred embodiment, the supply duct, an inlet of the throughput portion of the sensing element and a detector which is positioned inside the sensing element are essentially arranged along a common line. With this design of the device, reliable supply of essentially all fluid flowing through the device to the sensing element is ensured, thereby providing reliable sensing. It is also convenient to arrange a seal between the sensing element and the housing to prevent fluid that is to be sensed from passing outside the throughput portion of the sensing element.

In one embodiment, the sensing element is circular in shape and the throughput portion of the sensing element is arranged as a plurality of openings distributed in the circumferential direction. This design makes it possible for the sensing element to take in and sense fluid which flows from all directions around its circumference, whereby sensing will be safe and reliable.

It is preferred for the supply duct and the discharge duct to be arranged as a two-duct pipe, in which the ducts are separated by a wall arranged in the pipe. With the above design of the supply duct and the discharge duct, only one pipe has to be installed between the device and the object containing the fluid that is to be sensed.

The supply duct is suitably provided with an inlet facing a main flow direction of a fluid in the object that is to be sensed, and said discharge duct is suitably provided with an outlet positioned downstream of the inlet, said outlet suitably being positioned upstream of the downstream boundary of the two-duct pipe. The two-duct pipe thus allows a flow of fluid through the device to be formed when in said inlet an overpressure is generated and in said outlet a low pressure is generated, which results in a flow of fluid from the object that is to be sensed through the device.

It is thus made possible that a satisfactory partial amount of fluid in a main flow is allowed to be sensed by a sensing element by using a two-duct pipe which has relatively small dimensions. It is desirable to keep the dimensions of the two-duct pipe small so as to affect the main flow in the object as little as possible. The sufficient amount of diverted fluid to be sensed allows sensing that makes it possible to register the presence of particles and/or gases in the main flow which is to be sensed even in relatively small amounts. The registration of the presence of particles and/or gases in relatively small amounts in the main flow allows, in turn, sensing with good reliability and accuracy.

It has been found particularly convenient to arrange said outlet in an area where the lateral surfaces of the two-duct pipe relative to each other, in a direction away from said inlet, change from a divergent extent to a convergent extent relative to the main flow direction of the fluid in the object.

In one embodiment, at least one of the inlet and the outlet consists of at least one elongate opening, such as a slot. Such an elongate opening preferably has a width which is less than 5 mm, preferably 1-4 mm and in particular 2-3 mm. Moreover it is particularly convenient to arrange said elongate opening so as to extend along the major part of the portion of the two-duct pipe which in use is positioned inside said object. In an alternative embodiment, said elongate opening consists of a plurality of elongate openings, which are spaced from each other in the longitudinal direction of the two-duct pipe.

By arranging the inlet and/or the outlet as elongate openings, it has been found that the diverted partial amount of fluid from the main flow of fluid in the object advantageously consists of a relatively homogeneous mixture of fluid from essentially the entire extent of the elongate opening transversely to the object. Since withdrawal of fluid for sensing from essentially the entire cross-section of the object can be obtained in this manner, the risk decreases that only local areas of the fluid flowing in the object are sensed in terms of identification of particles and/or gases.

To allow identification of a flow flowing through the device after installation, a flow indicator is preferably arranged in the path of the fluid through said housing. In one embodiment such a flow indicator is arranged for visual reading. It is also possible to arrange a flow indicator which emits a signal that can be used, for instance, to display a message on an information panel or the like. In one embodiment, the indicator is formed as an element which is set in motion by the air flow when the device is correctly installed and a flow through the object that is to be sensed exists. Said indicator provides a simple visual confirmation that there is no substantial leakage and that fluid from the object really flows through the device.

It is preferred to arrange a filter somewhere in the path of the fluid between the object that is to be sensed and the sensing element. Said filter prevents any dirt particles in the fluid flowing through the device from entering the sensing element, which dirt particles may affect the operation of the sensing element. Furthermore said filter is preferably replaceably arranged to allow easy replacement when dirty.

In one embodiment, a fan is arranged in the path of the fluid through the device to enhance or produce a throughput of the fluid that is to be sensed. Such a fan is conveniently placed in the vicinity of the connection for the mouth of the discharge duct in the housing, but a person skilled in the art realises that the fan can be placed anywhere with maintained effect in the flow passage between the inlet and the outlet to the object containing the fluid that is to be sensed.

In one embodiment, the housing is provided with a connection space which is adapted to accommodate electrical connection components, which connection space is substantially shielded from the fluid which is intended to flow through the housing, a shield consisting of a printed circuit card which is adapted to carry the connection components. By arranging the connection space separated from the passing fluid, easy accessibility for installation and maintenance is ensured. It is also avoided that the connection components are subjected to any substantial influence from the fluid and any harmful substances in the same.

Preferably the first passage portion is visually and physically accessible through an at least partially transparent cover which can be removed and re-applied. For instance, the removable and re-applicable cover is arranged to engagingly cooperate with the housing by a bayonet coupling. By providing the device with a visually accessible portion, it is easy to inspect and check that the device is in good condition. By providing easy physical accessibility, it is also possible to perform service and maintenance with small efforts, for instance when exchanging the sensing element.

In one embodiment, the removable and re-applicable cover is provided with a closable measuring hole which allows access for testing the function of the device after installation. For example, a test spray can be injected through said measuring hole after installation to check that the device is correctly installed and emits a signal when sensing the test spray. It is also possible to use the measuring hole to perform a test of the fluid by means of a probe or the like, which is introduced through said measuring hole.

In one embodiment, said housing consists of two housing elements that are to be joined to each other. By forming the housing of two housing elements that are to be joined, easy manufacture of the inner and outer mould of the housing is ensured, which preferably are injection moulded from a polymer material. It will be appreciated that the parting of the two housing elements can be performed in a number of different ways. It will also be appreciated that the housing can be composed of more or fewer housing elements than two.

DETAILED DESCRIPTION OF PREFERRED EMBODIMENTS

The invention will now by way of example be described in more detail by means of embodiments and with reference to the accompanying drawings.

Figure 1:
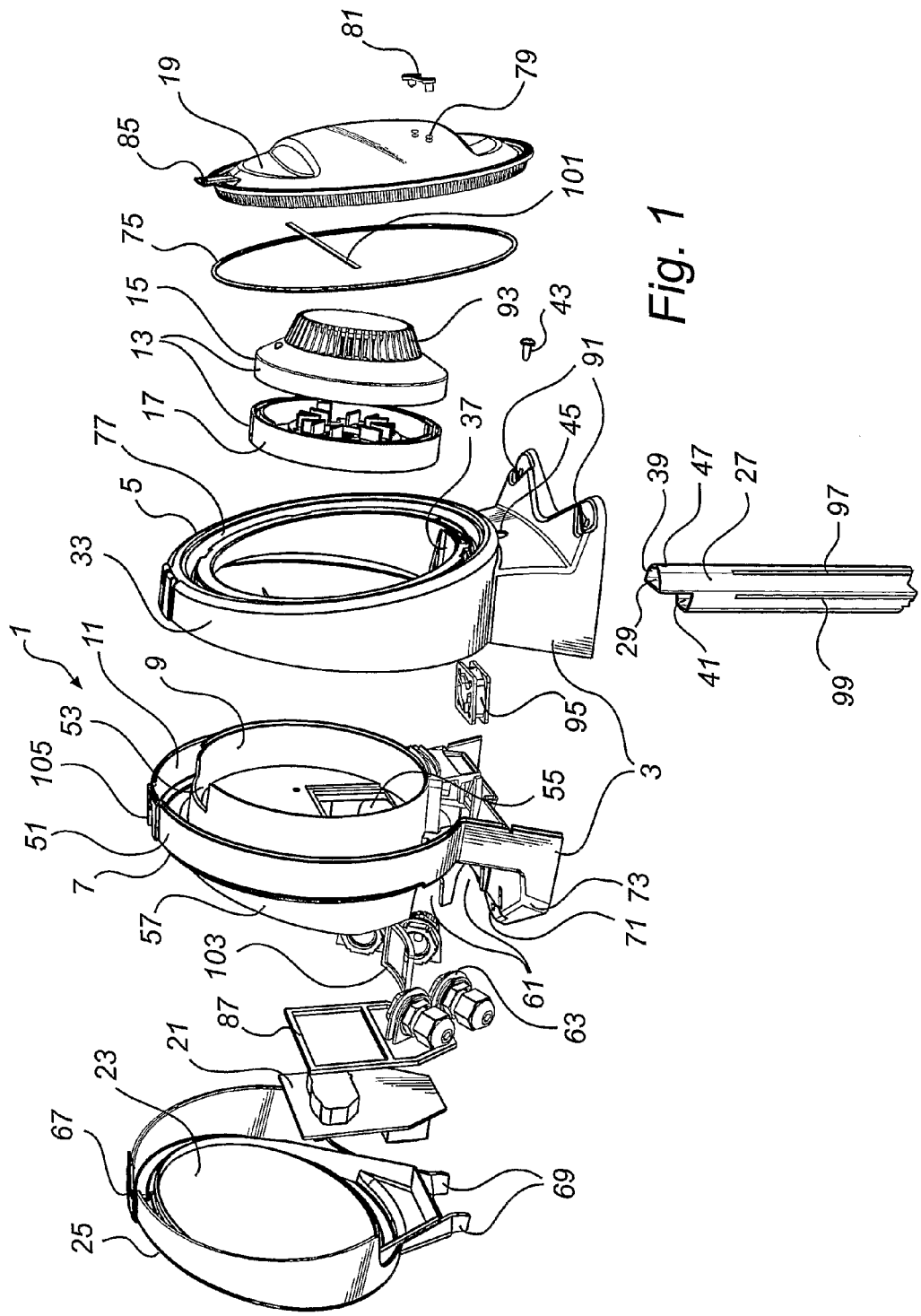
FIG. 1 is an exploded view in perspective of an embodiment of a device according to the invention for sensing a fluid.

FIG. 1 is an exploded view in perspective of a preferred embodiment according to the invention of the device 1 for sensing a fluid, for instance in a ventilation duct.

A preferred embodiment of the invention consists of a housing 3, which preferably consists of a front housing element 5 and a rear housing element 7. The front and rear housing elements 5, 7 are in the embodiment shown in FIG. 1 arranged to be joined to each other, to form in the joined state a housing 3 with a first space 9, which is a first passage portion, and a second space 11, which is a second passage portion, which spaces are substantially shielded from each other. A sensing element 13, which consists of a sensing part 15 and a connecting part 17, is arranged inside the first space 9. Furthermore the preferred embodiment of the device 1 as shown in FIG. 1 is provided with an at least partially transparent cover 19 which is formed to be able to close one side of the first space 9. The side, opposite to the cover 19, of the first space 9 is in the preferred embodiment closed by a printed circuit card 21 which is adapted to carry components that are used for the connection of the device 1 to, for instance, power supply, which components are mounted on a side of the printed circuit card 21 which faces away from the first space 9. A third space 23 which is shielded from the first and the second space 9, 11 is partially formed by a protective cover 25 which is arranged to cover and protect the components of the printed circuit card 21. Supply and discharge between the device and the object containing the fluid that is to be sensed is, according to a preferred embodiment as shown in FIG. 1, arranged by means of a two-duct pipe 27, in which the ducts are separated by a wall 29 arranged in the pipe.

In a preferred embodiment, the front housing element 5 is formed with a circular upper housing portion. From said circular housing portion extends a lower base portion, whose lower part preferably is formed as a foot which is intended for mounting of the device. A front part of the first space 9 is formed by a through hole in the front wall surface of the front housing element, a circular wall portion, which extends axially away from the periphery of the through hole, forming a shield 31 between the first space and the second space 11 positioned peripherally outside the first space 9. A front part of the second space 11 is defined radially outwards by a circular wall portion 33 which partly consists of a part of the outer wall portion of the front housing element 5.

In the preferred embodiment, the underside of the front housing element 5 is formed with a connection coupling 35 arranged to receive the two-duct pipe 27 which extends between the device 1 and the object containing the fluid that is to be sensed. The circular wall portion of the front housing element 5, which constitutes a wall portion of the shield 31 between the first and second spaces 9, 11, is provided with a bushing 37 which is adapted to communicate with a supply duct 39 in the two-duct pipe 27. Furthermore the second space 11 communicates with a discharge duct 41 of the two-duct pipe 27. The two-duct pipe 27 is adapted to be locked to the front housing element 5 by a fastening screw 43 which is inserted through a hole 45 in the front wall surface of the front housing element 5 to be received in a corresponding screw hole 47 in the two-duct pipe 27.

In a preferred embodiment, the rear housing element 7 is formed to be joined to the front housing element 5. Consequently also the rear housing element 7 is, like the front housing element 5, formed with a circular upper housing portion and, extending therefrom, a base portion with a lower part intended for mounting of the device.

From a surface of the rear housing element 7, a circular wall portion 49 extends towards the front housing element 5. The circular wall portion 49 corresponds to the shield of the front housing element 5 between the first space 9 and the second space 11 positioned peripherally outside the first space 9, the circular wall portions 31, 49 in the front and rear housing elements 5, 7 having substantially the same diameter.

Thus the circular wall portion 49 in the rear housing element 7 forms a shield between a rear part of the first space 9 and a rear part of the second space 11. Furthermore the rear part of the second space is defined radially outwards by a circular wall portion which constitutes part of the outer wall portion 51 of the rear housing element. The circular wall portion 49 in the rear housing element 7 is at its upper edge formed with a recess which constitutes a discharge opening 53 between the first and the second space 9, 11 in the assembled state of the device 1.

Moreover the rear wall surface of the rear housing element 7 is provided with a recess 55 which receives and is sealed by, for instance, a printed circuit card 21, which will be described in more detail below. The rear surface of the rear housing element 7 is, on the side facing away from the first and the second space 9, 11, further provided with a projecting wall portion 57, which constitutes part of a third space 23, which is intended to constitute a connection space for connection of electronics to the device 1. The projecting wall portion 57 is formed with four recesses 61 which constitute bushings for cables and the like, the recesses having a shape which can receive ordinary cable bushings and sealing plugs 63, such as membrane bushings. This connection space is closed by a removable protective cover 25 for protecting the electronics enclosed in the connection space. The protective cover 25 is formed with a locking means 67 which projects at the upper edge thereof and is formed with a through hole that is adapted to snap-lockingly engage a projection 105 which is arranged on the rear housing element 7. It will be appreciated that the protective cover can also be mounted on the rear housing element by other fastening means, such as screws. The lower edge of the protective cover 25 is provided with two projecting engaging means 69 which in the assembled position are received by two corresponding recesses 71 in a fixing lug 73 projecting from the rear housing element 7. In one embodiment, the protective cover 25 is at least partially made of a transparent material, such as polycarbonate (PC), to allow visual access to the electronics.

In a preferred embodiment, the circularly formed, at least partially transparent cover 19 is arranged to engage the front housing element 5 to close one side of the first space 9. The cover 19 is removable and re-applicable to allow access to the first space 9 to allow, when required, for instance replacement of the sensing element 13 or a filter 103 or other maintenance. A seal 75 is preferably arranged between the cover 19 and the front housing element 5 to provide tight-fitting engagement between the cover 19 and the front housing element 5. In a preferred embodiment, the seal 75 is arranged in a circular groove 77 in the front wall surface of the front housing element 5. In the embodiment shown in FIG. 1, the cover 19 is fixed to the first housing element by a bayonet coupling. However, it is possible to arrange the cover 19 on the housing 3 in other ways, for instance by screws, threads, clips, snap fits etc. In one embodiment the transparent cover 19 is made of polycarbonate (PC).

Furthermore the cover 19 is preferably also provided with a closable measuring hole 79 which allows access for testing the function of the device 1 after installation. In the embodiment illustrated, the measuring hole 79 is closable by a closing means 81 which preferably is designed so that, at the end opposite the part closing the measuring hole 7, it is connected to the cover 19, in which case the closing means 81 does not come loose from the cover 19 when opening the measuring hole 79. This reduces the risk of losing the closing means 81 when opening the measuring hole 79. In the embodiment illustrated, the cover 19 is also provided with projecting portions 83 which are adapted to provide a good grip when removing the cover from the front housing element and mounting it on the same. Furthermore, the at least partially transparent cover 19 is preferably provided with a locking lug 85 at its peripheral edge. The locking lug 85 has a through hole which is adapted to receive a locking screw (not shown), which is screwed into the front housing element 5 to lock the cover 19 in its direction of rotation relative to the front housing element 5.

In the assembled position of the device 1, the two housing elements 5, 7 described above are joined to each other so as to form the first space 9 and the second space 11 in the housing 3. These two spaces 9, 11 are substantially shielded from one another by the two circular wall portions 31, 49 in the respective housing elements 5, 7 being brought together and forming a shielding wall between the first space 9 and the second space 11. Furthermore the first and second spaces 9, 11 are shielded from the environment of the device 1 by the above-described transparent cover 19 and the sealing printed circuit card 21. Consequently two substantially closed spaces 9, 11 are formed, which means that fluid supplied to the device 1 will essentially flow between the supply duct 39 in the first space 9 and the discharge duct 41 in the second space 11 through said discharge opening 53, which is arranged in the circular shielding wall portion 49 of the rear housing element 7.

The two housing elements 5, 7 are preferably joined to each other by ultrasonic welding, but it should be noted that also other methods of joining can be used. For reasons of manufacture, it is preferred to form the housing 3 of said housing elements 5, 7. The housing elements 5, 7 are suitably made of a polymer material, such as Acrylonitrile-Butadiene-Styrene (ABS), by injection moulding.

In a preferred embodiment, the recess 55 in the rear wall surface of the housing element 7 is, as stated above, closed by, for instance, a printed circuit card 21. According to the embodiment in FIG. 1, a strip seal 87 of substantially the same extent as the peripheral edge of the printed circuit card 21 is arranged against the rear housing element, the printed circuit card 21 abutting against the strip seal 87 by a pressing force to provide a sealing effect between the printed circuit card 21 and the rear housing element 7. The printed circuit card 21 is fastened to the rear housing element 7 by, for instance, conventional fastening elements, such as screws, or by adhesive or the like. It is also possible to fasten the printed circuit card by, for instance, double-stick tape, in which case the tape can also act as the sealing element.

A guide 89 for the printed circuit card 21 is preferably arranged on the rear housing element 7. In a preferred embodiment according to FIG. 1, such a guide 89 is arranged as a guiding edge which projects around the printed circuit card 21 from the rear housing element 7. It is also possible to arrange the guide 89 in other manners, for instance as individual projecting portions or the like. It is preferred to arrange a guide also for the seal 87. In a preferred embodiment, the same guide is used for the seal 87 and for the printed circuit card 21. It is also possible, for instance, to arrange the guide for the seal 87 as a groove in the rear housing element 7.

In the preferred embodiment, the housing elements 5, 7 are preferably provided with a mounting portion which is intended for mounting of the device 1 adjacent to the object, for instance a ventilation duct, which contains the fluid that is to be sensed. It is preferred to arrange a fitting (not shown) on the object containing the fluid that is to be sensed, in which case the device 1 is mounted on this fitting which is positioned between the device 1 and the object. In the embodiment of the device 1 shown in FIG. 1, the front housing element is formed with two fastening through holes 91, which are arranged at the lower edge of each of the corners which are positioned in a direction away from the parting between the front and the rear housing element 5, 7. Furthermore the rear housing element 7 is formed with a fastening through hole 73, which is positioned at the lower edge substantially in the centre of the side oriented away from the parting between the front and the rear housing element 5, 7. Each fastening through hole 73, 91 is intended for a fastening screw (not shown). In a preferred embodiment, it is possible to place the device 1 in an optional position along the circumference of the object containing the fluid that is to be sensed, thereby providing great freedom as to the placing of the device 1.

Said mounting portions of the respective housing elements are preferably designed so that they jointly form the shape of an arrow when the front and rear housing elements are joined to each other. The purpose of this arrow is to visually indicate the location of the housing relative to the main flow direction of the fluid that is to be sensed in the object. Consequently, safe installation of the device is allowed, decreasing the risk of arranging the housing incorrectly relative to said main flow direction.

The sensing element 13, which is known per se, is in the preferred embodiment formed with a sensing part 15 comprising a detector, such as a smoke detector, and a connecting part 17, which can be released from each other by a turning motion of the sensing part 15 relative to the connecting part 17. The sensing part 15 is joined to the connecting part 17 by mechanically and electrically operating connecting means on the sensing part 15 being lockingly engaged with corresponding connecting means on the connecting part 17 in a locking rotary motion of the sensing part 15 relative to the connecting part 17. The connecting part 17 is preferably screwed to the rear housing element 7 of the housing 3. By removing the transparent cover 19 from the housing 3, the sensing part 15 can be exchanged in one simple operation, after which the cover 19 is again mounted on the housing 3. As a result, it is easy to maintain and service the device 1 in case of damage or wear.

The sensing element 13 shown in FIG. 1 is substantially circular in shape and is provided with flanges 93 in the circumferential direction which constitute a throughput portion for the fluid that is to be sensed.

In one embodiment a fan 95 is arranged in the second space 11, in the vicinity of the discharge duct 41 of the two-duct pipe 27, to enhance a throughput of the fluid that is to be sensed. It will be appreciated that it is possible to arrange such a fan 95 with maintained effect anywhere between the inlet and the outlet to the object containing the fluid that is to be sensed.

Said two-duct pipe 27, which comprises the supply duct 39 and the discharge duct 41, is preferably formed in one piece as an extruded pipe, preferably of aluminium. The pipe has a section transversely to the longitudinal direction where the peripheral shape of the circumferential surface that is to be oriented towards the flow is arched and the side which is adapted to be oriented along the flow has a substantially flat circumferential surface. Moreover the supply duct 39 and the discharge duct 41 at the end of the two-duct pipe 27 which is directed away from the housing 3 are closed by, for example, a plug-like element.

In a preferred embodiment, the two-duct pipe 27 is provided with an inlet 97 which is in fluid communication with the supply duct 39. In use, the inlet 97 is arranged in the vicinity of the upstream boundary of the two-duct pipe 27, so that the inlet 97 is substantially facing the main flow direction of the fluid flowing in the object. The orientation of the inlet

97 towards the main flow direction of the fluid in the object allows fluid to flow into the supply duct 39 of the two-duct pipe 27 for further transport to said sensing element 13 which is arranged inside said housing 3.

The two-duct pipe 27 is also provided with an outlet 99 which is in fluid communication with the discharge duct 41, which outlet 99 is positioned downstream of said inlet 97 and upstream of the downstream boundary of the two-duct pipe 27. It has surprisingly been found that the placing of the outlet 99 upstream of the downstream boundary of the two-duct pipe 27 results in a favourable throughput of the partial amount of fluid that is diverted from the object to be sensed by the sensing element 13 inside said housing 3.

In an alternative embodiment (not shown) the circumferential surface of the two-duct pipe 27 which is facing the flow direction of the fluid in the object is provided with a plurality of spaced-apart inlet holes which are distributed along the longitudinal direction of the two-duct pipe 27 and communicate with the supply duct 39. Furthermore the circumferential surface oriented along the flow direction is provided with spaced-apart outlet holes which are distributed along the longitudinal direction of the two duct-pipe 27 and communicate with the discharge duct 41.

The end of the two-duct pipe 27 which is adapted to be inserted into the housing 3 is formed so that the mouth of the supply duct 39 is positioned radially closer to the centre of the housing than the mouth of the discharge duct 41.

In a preferred embodiment, the front housing element 5, the rear housing element 7, the at least partially transparent cover 19 and the protective cover 25 are made of a polymer material. However, a person skilled in the art realises that these parts can be made of alternative materials without affecting the function of the device 1.

A flow indicator 101 is preferably arranged to be visually visible in the first passage portion of the front housing element 5. It will be appreciated, however, that a flow indicator 101 can be arranged anywhere in the flow passage between the inlet and the outlet of the object containing the fluid that is to be sensed. In one embodiment, the flow indicator 101 is formed as a thin foil-like band. Preferably one end of said foil-like band is attached to the transparent cover 19. When said flow indicator 101 is positioned inside the housing 3 in the flow passage of the fluid, the band is set in motion by the passing fluid. The movement of the band due to the flowing fluid provides a visually readable indication that fluid is flowing through the device 1.

In an alternative embodiment, the flow indicator 101 is designed as a slightly turned plate which is suspended by two torsion wires (not shown). The fluid flowing in the device 1 makes the plate oscillate, thereby providing a visually readable indication that fluid is flowing through the device 1. It is also possible to provide the device 1 with an electronic flow indicator, which for instance emits a signal indicating that a flow of fluid flows through the device.

In one embodiment, a replaceable filter 103 is preferably connected to the bushing 37 in the first passage portion 9 of the front housing element 11. The filter 103 is adapted to prevent dirt particles in the air flowing into the device from entering the sensing element. It will be appreciated that the filter can be arranged anywhere between the supply duct mouth in the object containing the fluid that is to be sensed and the sensing element. In the embodiment shown in FIG. 1, the filter 103 is retractably received between the supply duct mouth and the sensing element in grooves which are formed in the front housing element 5. According to an alternative embodiment it is possible to arrange the filter and/or the flow indicator in the retractably received part.

Figure 2:
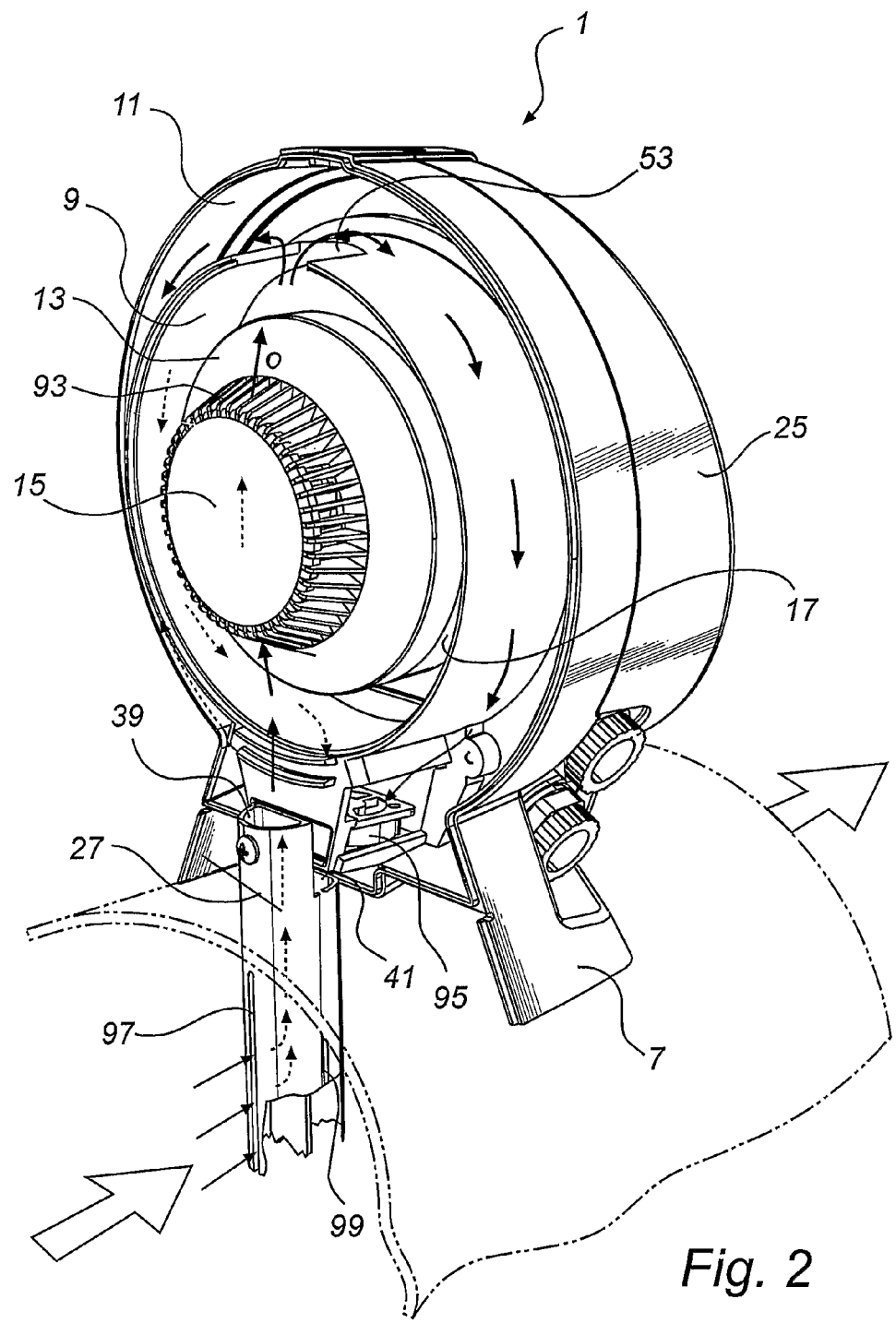
FIG. 2 is a perspective view of the device according to FIG. 1, where certain parts have been excluded to illustrate the path of the fluid through the device.
Figure 3:
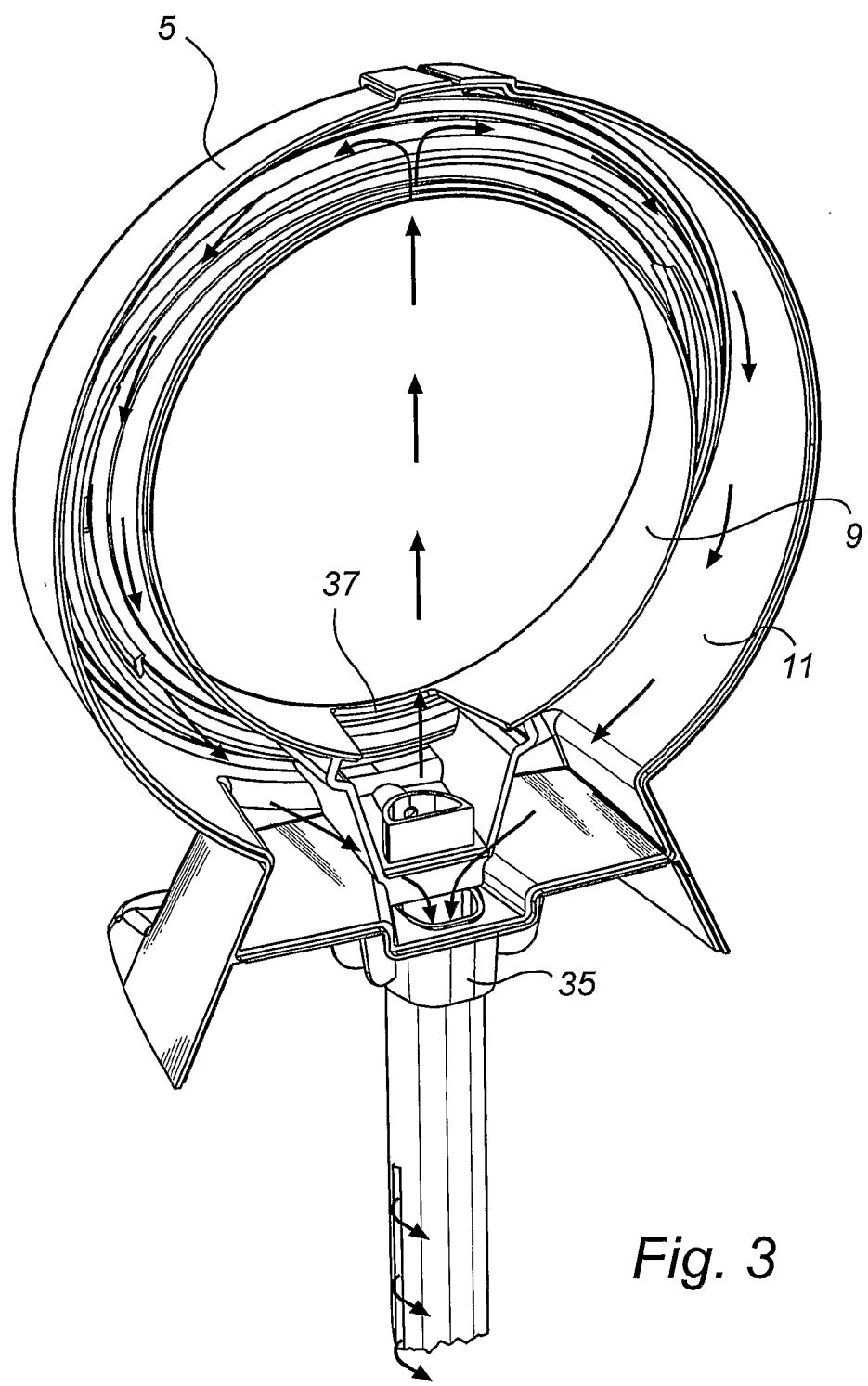
FIG. 3 is a perspective view of a front housing element of the device according to FIG. 1, where the path of the fluid is indicated by arrows.

FIGS. 2 and 3 show how the fluid diverted from the object, preferably a ventilation duct, flows through the device 1 according to a preferred embodiment. The two-duct pipe 27 is provided with said inlet 97 in the circumferential surface of the supply duct 39, said inlet 97 being oriented so that its mouth is oriented towards the flow of fluid in the object. The orientation of the inlet 97 relative to the flow of fluid allows fluid to flow into the supply duct 39. The fluid supplied to the supply duct 39 is then passed on to enter the device 1 through the recess 37 which is arranged to connect the mouth of the supply duct 39 to the first space 9 in the housing 3. The mouth of the supply duct 39 in the first space is positioned in the vicinity of the throughput portion of the sensing element 13 to allow a substantially directly directed flow of fluid towards the sensing part 15. The fluid supplied to the first space 9 of the housing 3 then enters through the flanges 93 which are arranged around the sensing part 15 to pass a detector, for instance a smoke detector, which is accommodated in the sensing part 15. Further the fluid flows out through the flanges 93 of the sensing part 15, on the substantially opposite side relative to the side where the fluid enters.

When the fluid supplied to the first space has passed the sensing part 15, the fluid flows into the second space 11 through the discharge opening 53 between the first space 9 and the second space 11. By the mouth of the supply duct 39 and the discharge opening 53 being substantially opposed to each other, with the sensing part 15 positioned between them, a large amount of the fluid supplied to the first space 9 will be forced to pass the sensing part 15, thus ensuring reliable sensing.

The fluid that has flown from the first space 9 to the second space 11 is passed on through the passage which is formed by the second space 11 and extends between the discharge opening 53 and the mouth of the discharge duct 41, the fluid flowing out from the second space 11 and into the discharge duct 41 of the two-duct pipe 27. The discharge duct 41 is further provided with said outlet 99 in the circumferential surface. Thus the fluid supplied to the discharge duct 41 flows out in the object through the outlet 99 arranged in the circumferential surface of the discharge duct 41.

By arranging the flow passage according to the device 1, a compact design which requires a small installation space is obtained. This is provided by the device having a short overall length in the flow direction of the fluid inside the object that is to be sensed. This short overall length is ensured by the fluid being arranged to flow through the device with a substantially transverse extent relative to the longitudinal direction of the object.

The device 1 for sensing a fluid can be used in a variety of fields. For instance, such a device can be used to sense a fluid to identify the possible presence of different kinds of particles and/or gases, such as flue gas, carbon dioxide, oxygen, carbon monoxide, laughing gas, hydrocarbons etc. The device can also be used to register, for example, the amount of moisture in a fluid or to register the temperature of a fluid. It will be appreciated by a person skilled in the art that with a device 1 it is also possible to simultaneously sense a plurality of the parameters stated above by way of example. Consequently what can be sensed by the device 1 is determined by the type of detector which is arranged in the sensing part 15.

According to an alternative embodiment (not shown) of the device for sensing fluid, the housing is formed as one housing element. The housing element formed in one piece comprises a housing with a first space, which constitutes a first passage portion, and a second space, which constitutes a second passage portion, which spaces are substantially shielded from one another. The housing element is provided with a wall portion which constitutes a shielding wall between the first and the second space. Similarly to that described above, the first and the second space communicate with each other via a discharge opening, which suitably is arranged in the shielding wall portion. An at least partially transparent cover is arranged to close one side of the first and the second space. The cover is suitably arranged to abut against and seal the shielding wall, thereby contributing to the shielding between the first and the second space. The cover can be attached to the housing by screws or the like. However, it will be appreciated that the cover can also be attached in alternative ways, such as by a bayonet coupling or by a snap-locking action. In addition to the alternative design of the housing element, this alternative embodiment suitably has functions and features as described for the embodiments according to FIGS. 1-3.

The invention claimed is:

1. A device configured to sense a fluid, comprising:
a sensing element;
a housing accommodating the sensing element; and
a supply duct and a discharge duct, which ducts at one end are configured to communicate with the housing and which ducts at the other end are configured to communicate with the fluid that is to be sensed,
wherein the housing is formed with a first passage portion for the fluid that is to be sensed,
the sensing element is positioned in the first passage portion,
the supply duct opens into said first passage portion,
the discharge duct is connected to a discharge opening formed in the first passage portion and positioned at a considerable peripheral distance from a mouth of said supply duct in the first passage portion, so that the fluid that is to be sensed is actively made to pass the sensing element, and
the housing is provided with a second passage portion which is shielded from the first passage portion and which extends between said discharge opening in the first passage portion and the discharge duct.

2. A device as claimed in claim 1, wherein the mouth of the supply duct in the first passage portion is facing a throughput portion of the sensing element.

3. A device as claimed in claim 1, wherein the mouth of the supply duct in the first passage portion is arranged in the vicinity of a throughput portion of the sensing element.

4. A device configured to sense a fluid, comprising:
a sensing element;
a housing accommodating the sensing element; and
a supply duct and a discharge duct, which ducts at one end are configured to communicate with the housing and which ducts at the other end are configured to communicate with the fluid that is to be sensed,
wherein the housing is formed with a first passage portion for the fluid that is to be sensed,
the sensing element is positioned in the first passage portion,
the supply duct opens into said first passage portion,
the discharge duct is connected to a discharge opening formed in the first passage portion and positioned at a considerable peripheral distance from a mouth of said supply duct in the first passage portion, so that the fluid that is to be sensed is actively made to pass the sensing element, and
wherein the housing is provided with a second passage portion which is arranged as a passage duct which extends peripherally outside the first passage portion from said discharge opening to said discharge duct.

5. A device as claimed in claim 1, wherein a mouth of the discharge duct is positioned in the vicinity of the mouth of said supply duct at a considerable peripheral distance from the discharge opening.

6. A device as claimed in claim 2, wherein the supply duct, an inlet of the throughput portion of the sensing element and a detector which is positioned inside the sensing element are essentially arranged along a common line.

7. A device as claimed in claim 1, wherein a seal is arranged between the sensing element and the housing to make fluid that is to be sensed pass the throughput portion of the sensing element.

8. A device as claimed in claim 1, wherein the sensing element is circular in shape and the throughput portion of the sensing element is arranged as a plurality of openings distributed in the circumferential direction.

9. A device as claimed in claim 1, wherein the supply duct and the discharge duct are arranged as a two-duct pipe, in which the ducts are separated by a wall arranged in the pipe.

10. A device as claimed in claim 9, wherein said supply duct is provided with an inlet facing a main flow direction of a fluid in the object that is to be sensed, and said discharge duct is provided with an outlet positioned downstream of the inlet, said outlet being positioned upstream of the downstream boundary of the two-duct pipe.

11. A device as claimed in claim 10, wherein said outlet is positioned in an area where the lateral surfaces of the two-duct pipe relative to each other, in a direction away from said inlet, change from a divergent extent to a convergent extent relative to the main flow direction of the fluid.

12. A device as claimed in claim 10, wherein at least one of the inlet and the outlet includes at least one elongated opening.

13. A device as claimed in claim 1, wherein a flow indicator is arranged in the path of the fluid through said housing (3).

14. A device as claimed in claim 1, wherein a filter is arranged in the path of the fluid between the object that is to be sensed and the sensing element.

15. A device as claimed in claim 1, wherein a fan is arranged in the path of the fluid through the device to enhance or produce a throughput of the fluid that is to be sensed.

16. A device as claimed in claim 1, wherein the housing is provided with a connection space which is adapted to accommodate electrical connection components, which connection space is substantially shielded from the fluid which is intended to flow through the housing, a shield consisting of a printed circuit card which is adapted to carry the connection components.

17. A device as claimed claim 1, wherein the first passage portion is visually and physically accessible through an at least partially transparent cover which can be removed and re-applied.

18. A device as claimed in claim 17, wherein the removable and re-applicable cover engagingly cooperates with the housing by a bayonet coupling.

19. A device as claimed in claim 18, wherein the removable and re-applicable cover is provided with a closable measuring hole which allows access for testing the function of the device after installation.

20. A device as claimed in claim 1, wherein said housing includes two housing elements that are to be joined to each other.

21. A device as claimed in claim 1, wherein the fluid is in a ventilation duct.

22. A device as claimed in claim 12, wherein said at least one elongated opening is a slot.

* * * * *